United States Patent
Han (10) Patent No.: US 10,434,965 B2
(45) Date of Patent: Oct. 8, 2019

(54) VEHICULAR SAFETY SEAT, CONTROLLER COUPLED WITH VEHICULAR SAFETY SEAT, AND VEHICULAR SAFETY SEAT SYSTEM

(71) Applicant: BOE TECHNOLOGY GROUP CO., LTD., Beijing (CN)

(72) Inventor: Yanling Han, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 3 days.

(21) Appl. No.: 15/533,455

(22) PCT Filed: Jan. 5, 2017

(86) PCT No.: PCT/CN2017/070275
§ 371 (c)(1),
(2) Date: Jun. 6, 2017

(87) PCT Pub. No.: WO2017/211080
PCT Pub. Date: Dec. 14, 2017

(65) Prior Publication Data
US 2018/0194307 A1  Jul. 12, 2018

(30) Foreign Application Priority Data
Jun. 8, 2016 (CN) .......................... 2016 1 0400423

(51) Int. Cl.
*B60R 16/037* (2006.01)
*B60N 2/26* (2006.01)
(Continued)

(52) U.S. Cl.
CPC ........ *B60R 16/037* (2013.01); *A61B 5/02055* (2013.01); *A61B 5/6893* (2013.01);
(Continued)

(58) Field of Classification Search
None
See application file for complete search history.

(56) References Cited

U.S. PATENT DOCUMENTS 6,393,348 B1   5/2002  Ziegler et al.
7,735,920 B2   6/2010  Hinze et al.
(Continued)

FOREIGN PATENT DOCUMENTS

CN   102874140 A   1/2013
CN   103043003 A   4/2013
(Continued)

OTHER PUBLICATIONS

English translation of Chinese Patent Application Pub. No. CN105150886A (Jun. 20, 2018).*
(Continued)

*Primary Examiner* — Jean Paul Cass
(74) *Attorney, Agent, or Firm* — Intellectual Valley Law, P.C.

(57) ABSTRACT

The present application discloses a vehicular safety seat for a passenger including a detector configured to detect a plurality of physiological parameters and a plurality of environmental parameters associated with the passenger; a first transmitter configured to transmit a first set of physiological and environmental parameters detected by the detector; a first receiver configured to receive a control signal for controlling at least one parameter from among the plurality of physiological and environmental parameters based on a determination that a monitored parameter in the first set of physiological and environmental parameters has a first value that exceeds a corresponding monitored parameter threshold value; and an adjustor configured to adjust at least one of the plurality of environmental parameters based on the control signal.

9 Claims, 4 Drawing Sheets

(51) Int. Cl.

| | | |
|---|---|---|
| *B60N 2/879* | (2018.01) | |
| *B60N 2/90* | (2018.01) | |
| *A61B 5/0205* | (2006.01) | |
| *A61B 5/00* | (2006.01) | |
| *B60N 2/00* | (2006.01) | |
| *B60N 2/56* | (2006.01) | |
| *A61B 5/024* | (2006.01) | |

(52) U.S. Cl.
CPC ............. *B60N 2/002* (2013.01); *B60N 2/26* (2013.01); *B60N 2/56* (2013.01); *B60N 2/879* (2018.02); *B60N 2/90* (2018.02); *A61B 5/024* (2013.01)

(56) References Cited

U.S. PATENT DOCUMENTS

| | | | | |
|---|---|---|---|---|
| 7,827,256 | B2* | 11/2010 | Phillips | G06F 8/656 |
| | | | | 709/220 |
| 9,020,697 | B2* | 4/2015 | Ricci | H04W 4/21 |
| | | | | 701/36 |
| 9,082,238 | B2* | 7/2015 | Ricci | G06F 21/31 |
| 9,082,239 | B2* | 7/2015 | Ricci | B60Q 1/00 |
| 9,121,717 | B1* | 9/2015 | Zhu | B60W 30/16 |
| 9,147,298 | B2* | 9/2015 | Ricci | B60Q 1/00 |
| 9,317,983 | B2* | 4/2016 | Ricci | H04W 4/21 |
| 9,373,207 | B2* | 6/2016 | Ricci | B60Q 1/00 |
| 9,378,601 | B2* | 6/2016 | Ricci | B60Q 1/00 |
| 9,384,609 | B2* | 7/2016 | Ricci | B60Q 1/00 |
| 9,412,273 | B2* | 8/2016 | Ricci | G06F 16/25 |
| 9,483,796 | B1* | 11/2016 | Blessman | G06Q 40/08 |
| 9,524,597 | B2* | 12/2016 | Ricci | H04W 4/21 |
| 9,535,497 | B2* | 1/2017 | Rose | G06F 3/013 |
| 9,536,361 | B2* | 1/2017 | Ricci | H04W 4/21 |
| 9,541,633 | B2* | 1/2017 | Rybski | G01S 7/4004 |
| 9,547,373 | B2* | 1/2017 | Hsiao | G06K 9/00845 |
| 9,575,007 | B2* | 2/2017 | Rao | G01N 21/88 |
| 9,646,439 | B2* | 5/2017 | Ricci | H04W 4/21 |
| 9,685,098 | B1* | 6/2017 | Kypri | G09B 19/167 |
| 9,716,964 | B1* | 7/2017 | Sheng | H04W 4/20 |
| 9,718,441 | B2* | 8/2017 | Cogill | B60R 25/30 |
| 9,787,818 | B2* | 10/2017 | Kwon | H04W 4/90 |
| 9,826,500 | B1* | 11/2017 | Boss | H04W 24/08 |
| 9,840,166 | B2* | 12/2017 | Taylor | B60N 2/002 |
| 9,855,817 | B2* | 1/2018 | Hsiao | B60K 11/04 |
| 9,883,209 | B2* | 1/2018 | Ricci | H04W 4/21 |
| 9,928,734 | B2* | 3/2018 | Newman | B60Q 5/005 |
| 9,937,860 | B1* | 4/2018 | Moradi-Pari | B60Q 9/008 |
| 9,946,906 | B2* | 4/2018 | Ricci | H04L 9/321 |
| 9,954,260 | B2* | 4/2018 | Ho | H01M 10/63 |
| 9,963,106 | B1* | 5/2018 | Ricci | B60R 25/2018 |
| 9,984,572 | B1* | 5/2018 | Newman | G06Q 10/02 |
| 10,118,696 | B1* | 11/2018 | Hoffberg | B64C 39/001 |
| 2003/0016124 | A1* | 1/2003 | Schmidt | B60R 21/01 |
| | | | | 340/425.5 |
| 2004/0119612 | A1* | 6/2004 | Chen | G08G 1/0104 |
| | | | | 340/995.13 |
| 2006/0132924 | A1* | 6/2006 | Mimran | G02B 27/01 |
| | | | | 359/630 |
| 2012/0197523 | A1* | 8/2012 | Kirsch | G01C 21/362 |
| | | | | 701/426 |
| 2013/0012179 | A1* | 1/2013 | Watkins | H04L 67/34 |
| | | | | 455/418 |
| 2014/0306826 | A1* | 10/2014 | Ricci | H04W 4/21 |
| | | | | 340/573.1 |
| 2014/0359272 | A1* | 12/2014 | Hiltunen | G09C 1/00 |
| | | | | 713/150 |

FOREIGN PATENT DOCUMENTS

| | | |
|---|---|---|
| CN | 204687876 U | 10/2015 |
| CN | 105015608 A | 11/2015 |
| CN | 105150886 A | 12/2015 |
| CN | 105266465 A | 1/2016 |
| CN | 105539217 A | 5/2016 |
| CN | 105539219 A | 5/2016 |
| CN | 205844794 U | 12/2016 |

OTHER PUBLICATIONS

English translation of Chinese Patent Pub. No. CN105539217A to Zheng et al. (Jun. 20, 2018).*

English translation of Chinese Patent Pub. No. CN 204687876U (Jun. 20, 2018).*

International Search Report & Written Opinion dated Mar. 30, 2017 regarding PCT/CN2017/070275.

First Office Action in the Chinese Patent Application No. 201610400423.1, dated Feb. 12, 2018; English translation attached.

* cited by examiner

VEHICULAR SAFETY SEAT, CONTROLLER COUPLED WITH VEHICULAR SAFETY SEAT, AND VEHICULAR SAFETY SEAT SYSTEM

CROSS-REFERENCE TO RELATED APPLICATION

This application is a national stage application under 35 U.S.C. § 371 of International Application No. PCT/CN2017/070275 filed Jan. 5, 2017, which claims priority to Chinese Patent Application No. 201610400423.1, filed Jun. 8, 2016, the contents of which are incorporated by reference in the entirety.

TECHNICAL FIELD

The present invention relates to vehicular smart apparatuses, more particularly, to a vehicular safety seat, a controller configured to be coupled with a vehicular safety seat, and a vehicular safety seat system.

BACKGROUND

Vehicular safety seats such as vehicular child safety seats are occupant restraint systems serving to protect the occupants in motor vehicles. They performed several basic functions. First, vehicular safety seats prevent occupants from being ejected from the vehicle during a crash accident. Second, vehicular safety seats minimize the effects of collisions with interior vehicular structures. Third, they also reduce the control of crash forces applied to the occupants. Vehicular safety seats have significantly enhanced the safety of the passengers, particularly infants and small children.

SUMMARY

In one aspect, the present invention provides a vehicular safety seat for a passenger, comprising a detector configured to detect a plurality of physiological parameters and a plurality of environmental parameters associated with the passenger, a first transmitter configured to transmit a first set of physiological and environmental parameters detected by the detector; a first receiver configured to receive a control signal for controlling at least one parameter from among the plurality of physiological and environmental parameters based on a determination that a monitored parameter in the first set of physiological and environmental parameters has a first value that exceeds a corresponding monitored parameter threshold value; and an adjustor configured to adjust at least one of the plurality of environmental parameters based on the control signal.

Optionally, the first transmitter is configured to transmit the first set of physiological and environmental parameters at every first time interval.

Optionally, the detector comprises a sound sensor for sensing a volume level of sound in the passenger's vicinity; and the first transmitter is configured to transmit the first set of physiological and environmental parameters when the volume level of sound in the passenger's vicinity exceeds a threshold volume level.

Optionally, the detector is configured to detect a second set of physiological and environmental parameters at a second time interval after the adjustor adjusts the at least one of the plurality of environmental parameters, and the first transmitter is configured to transmit the second set of physiological and environmental parameters.

Optionally, the adjustor is configured to continue adjusting the at least one of the plurality of environmental parameters based on a determination that the monitored parameter in the second set of physiological and environmental parameters has a second value that exceeds the corresponding monitored parameter threshold value, and is closer to the corresponding monitored parameter threshold value than the first value.

Optionally, the detector comprises one or more of a temperature sensor, a humidity sensor, a heart rate sensor, and a pressure sensor.

Optionally, the vehicular safety seat further comprises a head rest for supporting at least a portion of the passenger's head and neck, provided on a seat back of the vehicular safety seat; wherein the detector comprises a first temperature sensor configured to sense a skin temperature of the passenger, and a second temperature sensor configured to sense an ambient temperature; the first temperature sensor is on a first surface of the head rest configured to be at least partially in contact with the passenger's neck; and the second temperature sensor is on a second surface beside the first surface of the head rest configured to have no contact with the passenger.

Optionally, the adjustor comprises one or more of a temperature adjustor, a music player, a tension adjustor, and a dryer.

Optionally, the temperature adjustor comprises an air ventilating apparatus on a side surface of a seat back of the vehicular safety seat.

Optionally, the detector comprises a camera configured to obtain an image of the passenger.

In another aspect, the present invention provides a controller configured to be coupled with a vehicular safety seat described herein, the controller comprises a second receiver configured to receive from the first transmitter the first set of physiological and environmental parameters; a processor configured to compare the first set of physiological and environmental parameters with a set of threshold physiological and environmental parameters, and determine whether the monitored parameter in the first set of physiological and environmental parameters has the first value that exceeds the corresponding monitored parameter threshold value; and a second transmitter configured to transmit the control signal to the first receiver.

Optionally, the detector is configured to detect a second set of physiological and environmental parameters at a second time interval after the adjustor adjusts the at least one of the plurality of environmental parameters; the first transmitter is configured to transmit to the second receiver the second set of physiological and environmental parameters; the second receiver is configured to receive from the first transmitter the second set of physiological and environmental parameters; and the processor is configured to compare the second set of physiological and environmental parameters with the set of threshold physiological and environmental parameters, and determine whether any parameter in the second set of physiological and environmental parameters has a value that exceeds a corresponding threshold value.

Optionally, the processor is configured to compare the second set of physiological and environmental parameters with the set of threshold physiological and environmental parameters and the first set of physiological and environmental parameters, and determine whether the monitored parameter in the second set of physiological and environmental parameters has a second value that exceeds the corresponding monitored parameter threshold value and is closer to the corresponding monitored parameter threshold value than the first value.

Optionally, the second transmitter is configured to transmit an alarm signal when the second value that is not closer to the corresponding monitored parameter threshold value than the first value.

Optionally, the controller further comprises a display panel configured to display a current set of physiological and environmental parameters associated with the passenger, and an indication whether any parameter in the current set of physiological and environmental parameters exceeds a corresponding threshold value.

Optionally, the controller is integrated into a mobile apparatus or a vehicle-mounted electronic system.

In another aspect, the present invention provides a vehicular safety seat system, comprising a vehicular safety seat and a controller, wherein the vehicular safety seat comprises a detector, a first transmitter, a first receiver, and an adjustor; the controller comprises a second receiver, a processor, and a second transmitter; the detector is configured to detect a plurality of physiological parameters and a plurality of environmental parameters associated with the passenger; the first transmitter is configured to transmit to the second receiver a first set of physiological and environmental parameters detected by the detector; the first receiver configured to receive from the second transmitter a control signal for controlling at least one parameter from among the plurality of physiological and environmental parameters based on a determination that a monitored parameter in the first set of physiological and environmental parameters has a first value that exceeds a corresponding threshold value; the adjustor is configured to adjust at least one of the plurality of environmental parameters based on the control signal; the second receiver is configured to receive from the first transmitter the first set of physiological and environmental parameters detected by the detector of the vehicular safety seat; the processor is configured to compare the first set of physiological and environmental parameters with a set of threshold physiological and environmental parameters, and determine whether the monitored parameter in the first set of physiological and environmental parameters has the first value that exceeds the corresponding monitored parameter threshold value; and the second transmitter is configured to transmit the control signal to the first receiver.

Optionally, the detector is configured to detect a second set of physiological and environmental parameters at a second time interval after the adjustor adjusts the at least one of the plurality of environmental parameters; the first transmitter is configured to transmit to the second receiver the second set of physiological and environmental parameters; the second receiver is configured to receive from the first transmitter the second set of physiological and environmental parameters; and the processor is configured to compare the second set of physiological and environmental parameters with the set of threshold physiological and environmental parameters, and determine whether any parameter in the second set of physiological and environmental parameters has a value that exceeds a corresponding threshold value.

Optionally, the processor is configured to compare the second set of physiological and environmental parameters with the set of threshold physiological and environmental parameters and the first set of physiological and environmental parameters, and determine whether the monitored parameter in the second set of physiological and environmental parameters has a second value that exceeds the corresponding monitored parameter threshold value and is closer to the corresponding monitored parameter threshold value than the first value.

Optionally, the adjustor is configured to continue adjusting the at least one of the plurality of environmental parameters when the second value exceeds the corresponding monitored parameter threshold value and is closer to the corresponding monitored parameter threshold value than the first value.

BRIEF DESCRIPTION OF THE FIGURES

The following drawings are merely examples for illustrative purposes according to various disclosed embodiments and are not intended to limit the scope of the present invention.

DETAILED DESCRIPTION

The disclosure will now be described more specifically with reference to the following embodiments. It is to be noted that the following descriptions of some embodiments are presented herein for purpose of illustration and description only. It is not intended to be exhaustive or to be limited to the precise form disclosed.

It is typically required by law that infants and small children to be restrained while they are in an operating motor vehicle. Accordingly, vehicular safety seats for children have been widely used. Typically, the vehicular safety seats are placed in the back seat of the moving vehicle to ensure the safety of the children. However, when the vehicle is in an operating state, it is inconvenient for a driver or a front seat passenger to monitor the children's status. Particularly, when the vehicle is moving in a highway, the driver cannot stop the vehicle to provide care to the children in the vehicular safety seats until the vehicle exits the highway. Thus, it is impossible for the driver to adjust the microenvironment of the children while driving.

Accordingly, the present invention provides, inter alia, a vehicular safety seat, a controller configured to be coupled with a vehicular safety seat, and a vehicular safety seat system that substantially obviate one or more of the problems due to limitations and disadvantages of the related art. In one aspect, the present disclosure provides a vehicular safety seat for a passenger. In some embodiments, the vehicular safety seat includes a detector configured to detect a plurality of physiological parameters and a plurality of environmental parameters associated with the passenger; a first transmitter configured to transmit a first set of physiological and environmental parameters detected by the detector; a first receiver configured to receive a control signal for controlling at least one parameter from among the plurality of physiological and environmental parameters based on a determination that a monitored parameter in the first set of physiological and environmental parameters has a first value that exceeds a corresponding monitored parameter threshold value; and an adjustor configured to adjust at least one of the plurality of environmental parameters based on the control signal.

Figure 1:
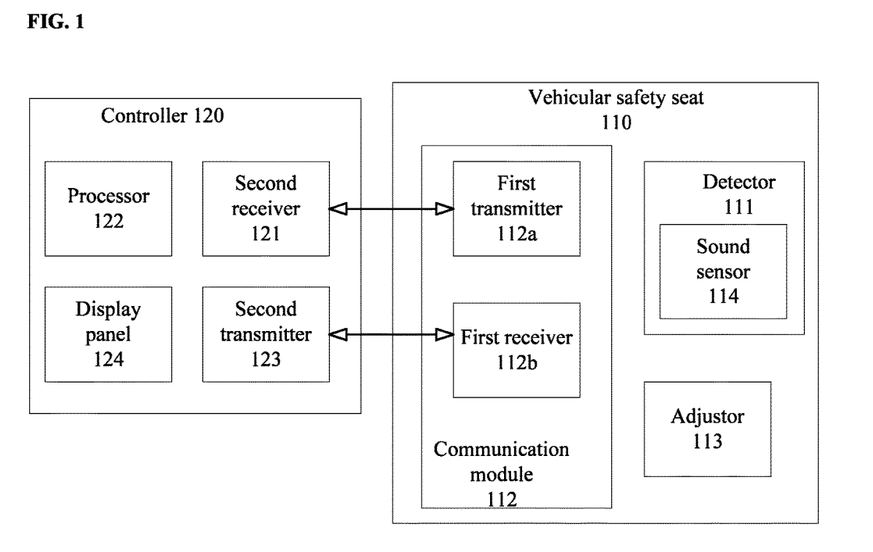
FIG. 1 is a block diagram illustrating the structure of a vehicular safety seat system in some embodiments according to the present disclosure.

FIG. 1 is a block diagram illustrating the structure of a vehicular safety seat system in some embodiments according to the present disclosure. Referring to FIG. 1, the vehicular safety seat system 100 in some embodiments includes a vehicular safety seat 110 and a controller 120. The vehicular safety seat 110 includes a detector 11, a communication module 112 (including a first transmitter 112a and a first receiver 112b), and an adjuster 113. Optionally, the detector 111 includes a sound sensor 114. The communication module 112 is configured to be communicably coupled to the detector 111, the adjustor 113, and the sound sensor 114.

In some embodiments, the detector 111 is configured to detect at least one health parameter associated with the passenger. The health parameter may be a physiological parameter of the passenger. Optionally, the health parameter may be an environmental parameter of the environment surrounding the passenger. Optionally, the detector 111 is configured to detect a plurality of physiological parameters and a plurality of environmental parameters associated with the passenger. Optionally, the passenger is an infant or a child, and the vehicular safety seat is a vehicular safety infant seat or child seat. Optionally, the passenger is a patient or a person with a disability, and the vehicular safety seat is specially designed seat. Optionally, the vehicular safety seat is a regular car seat installed in a car.

Optionally, the detector 111 includes one or more of a temperature sensor, a humidity sensor, a heart rate sensor, a pressure sensor, and a sound sensor. Optionally, the physiological parameter of the passenger includes one or more of a skin temperature of the passenger detected by a temperature sensor and a heart rate of the passenger detector by a heart rate sensor. Optionally, the environmental parameter includes one or more of an ambient temperature surrounding the passenger detected by a temperature sensor, a humidity detected by a humidity sensor, a tension (e.g., a seat belt tension) detected by a pressure sensor. Optionally, the humidity sensor is configured to detect a humidity caused by a diaper worn by an infant, and the humidity sensor may be disposed on a seat cushion of the vehicular safety seat. Optionally, the pressure sensor is configured to detect a tension of a seat belt, e.g., when worn by the passenger.

In some embodiments, the first transmitter 112a is configured to transmit a first set of physiological and environmental parameters detected by the detector, e.g., to the second receiver 121 in the controller 120. Optionally, the first transmitter 112a is configured to transmit the first set of physiological and environmental parameters at every first time interval (e.g., every 5 minutes, every 10 minutes, every 30 minutes, etc.). In some embodiments, the first receiver 112b is configured to receive a control signal for controlling at least one parameter from among the plurality of physiological and environmental parameters based on a determination that a monitored parameter in the first set of physiological and environmental parameters has a first value that exceeds a corresponding monitored parameter threshold value.

In some embodiments, the adjustor 113 is configured to adjust at least one of the plurality of environmental parameters based on the control signal.

In some embodiments, the detector 111 is configured to detect a second set of physiological and environmental parameters at a second time interval after the adjustor 113 adjusts the at least one of the plurality of environmental parameters. The first transmitter 112a is configured to transmit the second set of physiological and environmental parameters, e.g., to the second receiver 121 in the controller 120. The second set of physiological and environmental parameters are compared to the first set of physiological and environmental parameters to determine whether the physiological or environmental parameters associated with the passenger are improved by the adjustment.

In some embodiments, the adjustor 113 is configured to continue adjusting the at least one of the plurality of environmental parameters, e.g., when the physiological or environmental parameters associated with the passenger are improved by the adjustment. For example, the adjustor 113 may be configured to continue adjusting the at least one of the plurality of environmental parameters based on a determination that the monitored parameter in the second set of physiological and environmental parameters has a second value that still exceeds the corresponding monitored parameter threshold value, but is closer to the corresponding monitored parameter threshold value than the first value.

In some embodiments, the sound sensor 114 is configured to sense a volume level of sound in the passenger's vicinity (e.g., a volume level of a child's crying sound). The first transmitter 112a is configured to transmit the first set of physiological and environmental parameters when the volume level of sound in the passenger's vicinity exceeds a threshold volume level.

Optionally, the vehicular safety seat 110 further includes a battery configured to provide power to various components of the vehicular safety seat 110. The battery may be a rechargeable battery. Optionally, the battery is a vehicle-mounted battery.

Optionally, the communication module 112 (including the first transmitter 112a and the first receiver 112b) transmits data wirelessly. Optionally, the communication module 112 (including the first transmitter 112a and the first receiver 112b) transmits data through wires.

In some embodiments, the adjustor 113 includes one or more of a temperature adjustor, a music player, a tension adjustor, and a dryer. Various appropriate temperature adjustors may be used in the present adjustor 113. For example, the temperature adjustor may include an air ventilating apparatus for providing a zone of heated air or cooled air to the passenger. Optionally, the temperature adjustor is installed on a side surface of a seat back of the vehicular safety seat. In one example, the music player is configured to play soothing music or sound to calm down the passenger. In another example, the tension adjustor is configured to adjust the tension of the seat belt to provide a comfortable fit of the seat belt to the passenger. In another example, the dryer is configured to dry a vicinity of the seat cushion, e.g., when the diaper worn by an infant is wet.

Referring to FIG. 1, the controller 120 in some embodiments includes a second receiver 121, a processor 122, and a second transmitter 123. Optionally, the controller 120 further includes a display panel 124. The processor 122 is configured to be communicably coupled to the second receiver 121, the second transmitter 123, and the display panel 124.

In some embodiments, the second receiver 121 is configured to receive, e.g., from the first transmitter, the first set of physiological and environmental parameters. The processor 122 is configured to compare the first set of physiological and environmental parameters with a set of threshold physiological and environmental parameters, and determine whether the monitored parameter in the first set of physiological and environmental parameters has the first value that exceeds the corresponding monitored parameter threshold value. The second transmitter 123 is configured to transmit the control signal, e.g., to the first receiver 112*b*. Optionally, the second transmitter 123 is configured to transmit an alert signal to the driver, indicating that the passenger is not in a comfortable status, e.g., one or more monitored parameter exceeds the corresponding monitored parameter threshold value.

In some embodiments, the second receiver 121 is configured to receive, e.g., from the first transmitter 112*a*, the second set of physiological and environmental parameters. The processor 122 is configured to compare the second set of physiological and environmental parameters with the set of threshold physiological and environmental parameters, and determine whether any parameter in the second set of physiological and environmental parameters has a value that exceeds a corresponding threshold value.

In some embodiments, the processor 122 is further configured to determine whether the physiological or environmental parameters associated with the passenger are improved by the adjustment. For example, the processor 122 may be configured to compare the second set of physiological and environmental parameters with the set of threshold physiological and environmental parameters and the first set of physiological and environmental parameters, and determine whether the monitored parameter in the second set of physiological and environmental parameters has a second value that still exceeds the corresponding monitored parameter threshold value but is closer to the corresponding monitored parameter threshold value than the first value. When the physiological or environmental parameters associated with the passenger are not improved by the adjustment, e.g., when the second value that is not closer to the corresponding monitored parameter threshold value than the first value, the second transmitter 123 is configured to transmit an alarm signal, e.g., to a driver or another passenger. The alarm signal provides indication that the physiological or environmental parameters associated with the passenger are not improved by the adjustment. Upon receiving the alarm signal, the driver or another passenger may personally examine the physiological or environmental parameters associated with the passenger, and may choose to stop the vehicle. Optionally, for example, if the driver ignores the alarm, the processor is configured to continue transmitting a control signal for controlling the adjustor 113 to adjust at least one of the plurality of environmental parameters.

Optionally, the display panel 124 is configured to display a current set of physiological and environmental parameters associated with the passenger, and an indication whether any parameter in the current set of physiological and environmental parameters exceeds a corresponding threshold value.

Optionally, the controller 120 further includes a setting apparatus for setting the threshold physiological and environmental parameters or a range of allowable physiological and environmental parameters. The threshold physiological and environmental parameters or the range of allowable physiological and environmental parameters may be used to compare with the first set of physiological and environmental parameters or the second set of physiological and environmental parameters, to determine whether the passenger is in a comfortable state. Optionally, the setting apparatus is a remote control. Optionally, the setting apparatus is integrated into a vehicle-mounted electronic system. Optionally, the controller 120 further includes a memory for storing the threshold physiological and environmental parameters or the range of allowable physiological and environmental parameters, and the detected physiological and environmental parameters received from the vehicular safety seat 110.

Optionally, the controller 120 is integrated (e.g., partially or entirely) into a mobile apparatus (e.g., a mobile phone). The mobile apparatus may be placed at any appropriate position in the vehicle, e.g., based on the driver's preference. Optionally, the controller 120 is integrated into a vehicle-mounted electronic system. In one example, the controller 120 is integrated into a vehicle-mounted electronic system disposed in a center console of the vehicle.

Figure 2:
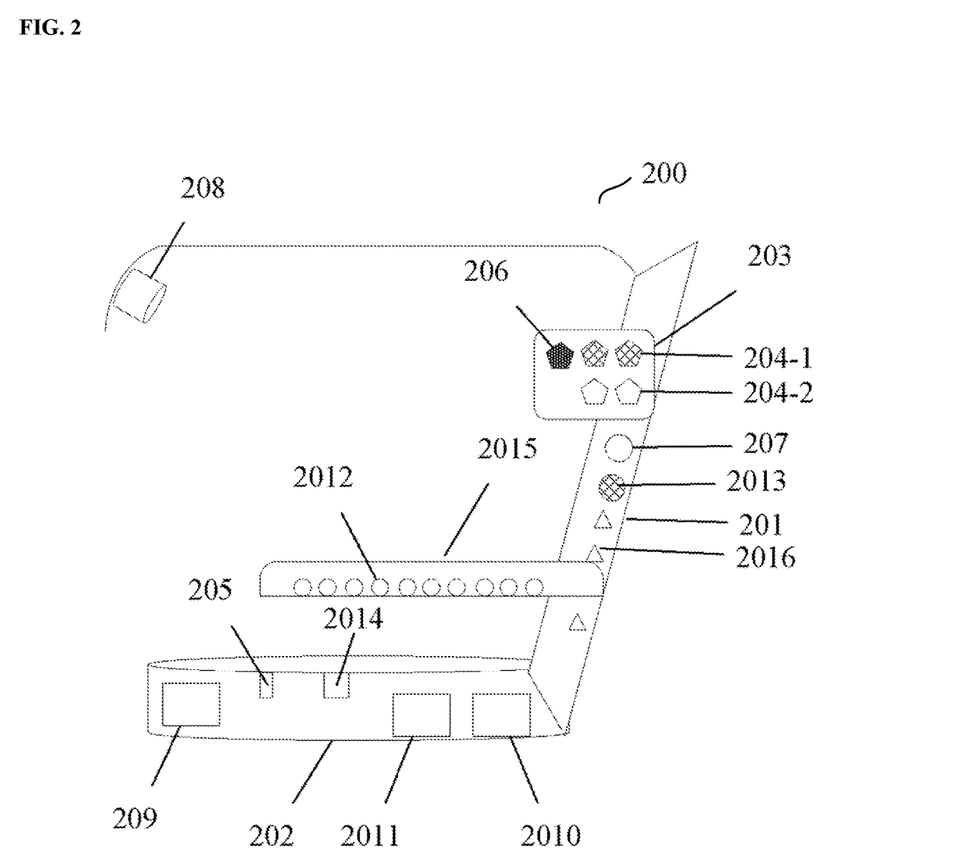
FIG. 2 is a schematic diagram illustrating the structure of a vehicular safety seat in some embodiments according to the present disclosure.

FIG. 2 is a schematic diagram illustrating the structure of a vehicular safety seat in some embodiments according to the present disclosure. Referring to FIG. 2, the vehicular safety seat 200 in some embodiments includes a seat back 201 and a seat base 202. The vehicular safety seat 200 further includes a head rest 203 for supporting at least a portion of the passenger's head and neck, provided on a seat back 201 of the vehicular safety seat 200. Moreover, the vehicular safety seat 200 includes a detector, e.g., one or more of a temperature sensor, a humidity sensor, a heart rate sensor, a pressure sensor, and a sound sensor. As shown in FIG. 2, the detector includes a first temperature sensor 204-1 configured to sense a surface temperature of the passenger, and a second temperature sensor 204-2 configured to sense an ambient temperature. Optionally, the first temperature sensor 204-1 is on a front surface of the head rest 203 configured to be at least partially in contact with the passenger's neck when the passenger occupies the vehicular safety seat, to measure the skin temperature of the passenger. Optionally, the second temperature sensor 204-2 is on a side surface of the head rest 203 configured to have no contact with the passenger when the passenger is sitting on the vehicular safety seat 200. The detector further includes a humidity sensor 205 disposed on a seat cushion of the vehicular safety seat. Optionally, the humidity sensor 205 is configured to detect a humidity caused by a diaper worn by an infant. The detector further includes a heart rate sensor 206 configured to monitor a heart rate of the passenger when the passenger occupies the vehicular safety seat. Optionally, the heart rate sensor 206 is disposed on the front surface of the head rest 203 configured to be at least partially in contact with the passenger's neck when the passenger occupies the vehicular safety seat. Optionally, the heart rate sensor 206 may be disposed on any position configured to be at least partially in contact with a passenger's body part where a heart rate can be measured, when the passenger occupies the vehicular safety seat. The detector further includes a pressure sensor 207 configured to detect a tension of a seat belt, e.g., when worn by the passenger. Optionally, the pressure sensor 207 is disposed on the seat back 201 at a position that is pressed upon when the seat belt is worn by the passenger. Optionally, the pressure sensor 207 is disposed on any position configured to be pressed upon when the seat belt is worn by the passenger. The detector further includes a camera 208 configured to obtain an image of the passenger so that a driver may monitor the passenger's activity in the vehicular safety seat 200. Optionally, the camera 208 is disposed at a position having a top front view of the vehicular safety seat 200, as shown in FIG. 2.

Referring to FIG. 2, the vehicular safety seat 200 in some embodiments further includes a communication module 209, a sound sensor 210, a temperature adjustor 2011, a music player 2012, a tension adjustor 2013, a dryer 2014, and an air ventilating apparatus 2016. The communication module 209, the sound sensor 210, the temperature adjustor 2011, the music player 2012, the tension adjustor 2013, the dryer 2014, and the air ventilating apparatus 2016 may be disposed at any appropriate positions of the vehicular safety seat 200. Optionally, the music player is disposed on an arm rest 2015 of the vehicular safety seat 200. The tension adjustor 2013 is configured to be coupled to, and be operated in coordination with, the seat belt. Optionally, the dryer 2014 is disposed on the seat base 202 of the vehicular safety seat 200, e.g., on the seat cushion of the vehicular safety seat 200 and configured to dry a vicinity of the seat cushion when the diaper worn by an infant is wet. Optionally, the air ventilating apparatus 2016 is disposed on a side surface of the seat back, ventilating an air flow along a direction away from the passenger and the temperature sensors 204-1 and 204-2.

In another aspect, the present disclosure provides a vehicular safety seat system having a vehicular safety seat and a controller. The vehicular safety seat includes a detector, a first transmitter, a first receiver, and an adjuster. The controller includes a second receiver, a processor, and a second transmitter. In some embodiments, the detector is configured to detect a plurality of physiological parameters and a plurality of environmental parameters associated with the passenger; the first transmitter is configured to transmit to the second receiver a first set of physiological and environmental parameters detected by the detector; the first receiver configured to receive from the second transmitter a control signal for controlling at least one parameter from among the plurality of physiological and environmental parameters based on a determination that a monitored parameter in the first set of physiological and environmental parameters has a first value that exceeds a corresponding threshold value; the adjustor is configured to adjust at least one of the plurality of environmental parameters based on the control signal; the second receiver is configured to receive from the first transmitter the first set of physiological and environmental parameters detected by the detector of the vehicular safety seat; the processor is configured to compare the first set of physiological and environmental parameters with a set of threshold physiological and environmental parameters, and determine whether the monitored parameter in the first set of physiological and environmental parameters has the first value that exceeds the corresponding monitored parameter threshold value; and the second transmitter is configured to transmit the control signal to the first receiver.

In some embodiments, the detector is configured to detect a second set of physiological and environmental parameters at a second time interval after the adjustor adjusts the at least one of the plurality of environmental parameters; the first transmitter is configured to transmit to the second receiver the second set of physiological and environmental parameters; the second receiver is configured to receive from the first transmitter the second set of physiological and environmental parameters; and the processor is configured to compare the second set of physiological and environmental parameters with the set of threshold physiological and environmental parameters, and determine whether any parameter in the second set of physiological and environmental parameters has a value that exceeds a corresponding threshold value.

In some embodiments, the processor is configured to compare the second set of physiological and environmental parameters with the set of threshold physiological and environmental parameters and the first set of physiological and environmental parameters, and determine whether the monitored parameter in the second set of physiological and environmental parameters has a second value that exceeds the corresponding monitored parameter threshold value and is closer to the corresponding monitored parameter threshold value than the first value.

In some embodiments, the adjustor is configured to continue adjusting the at least one of the plurality of environmental parameters when the second value exceeds the corresponding monitored parameter threshold value and is closer to the corresponding monitored parameter threshold value than the first value.

Optionally, the second transmitter is configured to transmit an alarm signal when the second value that is not closer to the corresponding monitored parameter threshold value than the first value. Optionally, the controller further includes a display panel configured to display a current set of physiological and environmental parameters associated with the passenger, and an indication whether any parameter in the current set of physiological and environmental parameters exceeds a corresponding threshold value.

Optionally, the vehicular safety seat system further includes a vehicle-mounted electronic system in a vehicle. Optionally, the controller is integrated into a vehicle-mounted electronic system. Optionally, the vehicular safety seat system further includes a mobile apparatus, and the controller is integrated into the mobile apparatus.

Figure 3:
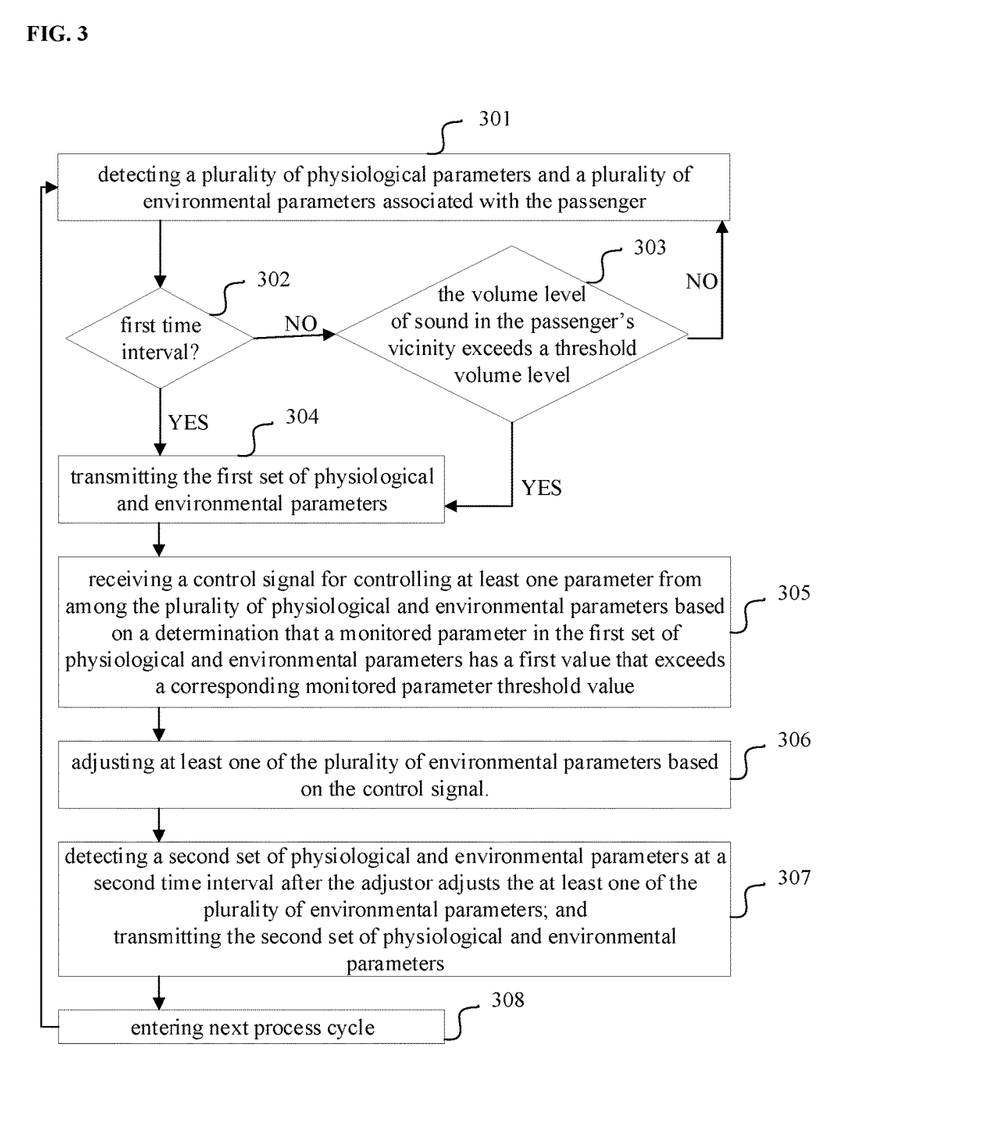
FIG. 3 is a flow chart illustrating the operating process of a vehicular safety seat in some embodiments according to the present disclosure.

FIG. 3 is a flow chart illustrating the operating process of a vehicular safety seat in some embodiments according to the present disclosure. Referring to FIG. 3, the operating process first includes a step 301 of detecting a plurality of physiological parameters and a plurality of environmental parameters associated with the passenger. Optionally, the physiological parameter of the passenger includes one or more of a skin temperature of the passenger detected by a temperature sensor and a heart rate of the passenger detector by a heart rate sensor. Optionally, the environmental parameter includes one or more of an ambient temperature surrounding the passenger detected by a temperature sensor, a humidity detected by a humidity sensor, a tension (e.g., a seat belt tension) detected by a pressure sensor. Optionally, the humidity is a humidity caused by a diaper worn by an infant. Optionally, the pressure is caused a tension of a seat belt, e.g., when worn by the passenger.

Next, the process includes a determination step 302 of determining whether a first time interval has been reached. If the first time interval has been reached, the process further includes a step of transmitting the first set of physiological and environmental parameters. If the first time interval has not been reached, the process further includes a determination step 303 of determining whether the volume level of sound in the passenger's vicinity exceeds a threshold volume level, e.g., whether the volume level of a child's crying sound exceeds a threshold volume level. If the volume level of sound in the passenger's vicinity exceeds the threshold volume level, the process includes a step 304 of transmitting the first set of physiological and environmental parameters.

Subsequently, the process further includes a step 305 of receiving a control signal for controlling at least one parameter from among the plurality of physiological and environmental parameters based on a determination that a monitored parameter in the first set of physiological and environmental parameters has a first value that exceeds a corresponding monitored parameter threshold value, and a step 306 of adjusting at least one of the plurality of environmental parameters based on the control signal.

Optionally, the process further includes a step 307 of detecting a second set of physiological and environmental parameters at a second time interval after the adjustor adjusts the at least one of the plurality of environmental parameters; and transmitting the second set of physiological and environmental parameters. Optionally, the second time interval is substantially the same as the first time interval.

Optionally, the process includes a step 308 of entering the next process cycle, e.g., repeating one or more steps described above.

Optionally, the plurality of physiological parameters and the plurality of environmental parameters detected and transmitted in the present process may be tagged. For example, each type of physiological parameters is tagged by a different tag, and each type of environmental parameters is tagged by a different tag. Moreover, a parameter from the first set of physiological and environmental parameters may be further distinguished from a parameter from the second set of physiological and environmental parameters by using different tags.

Figure 4:
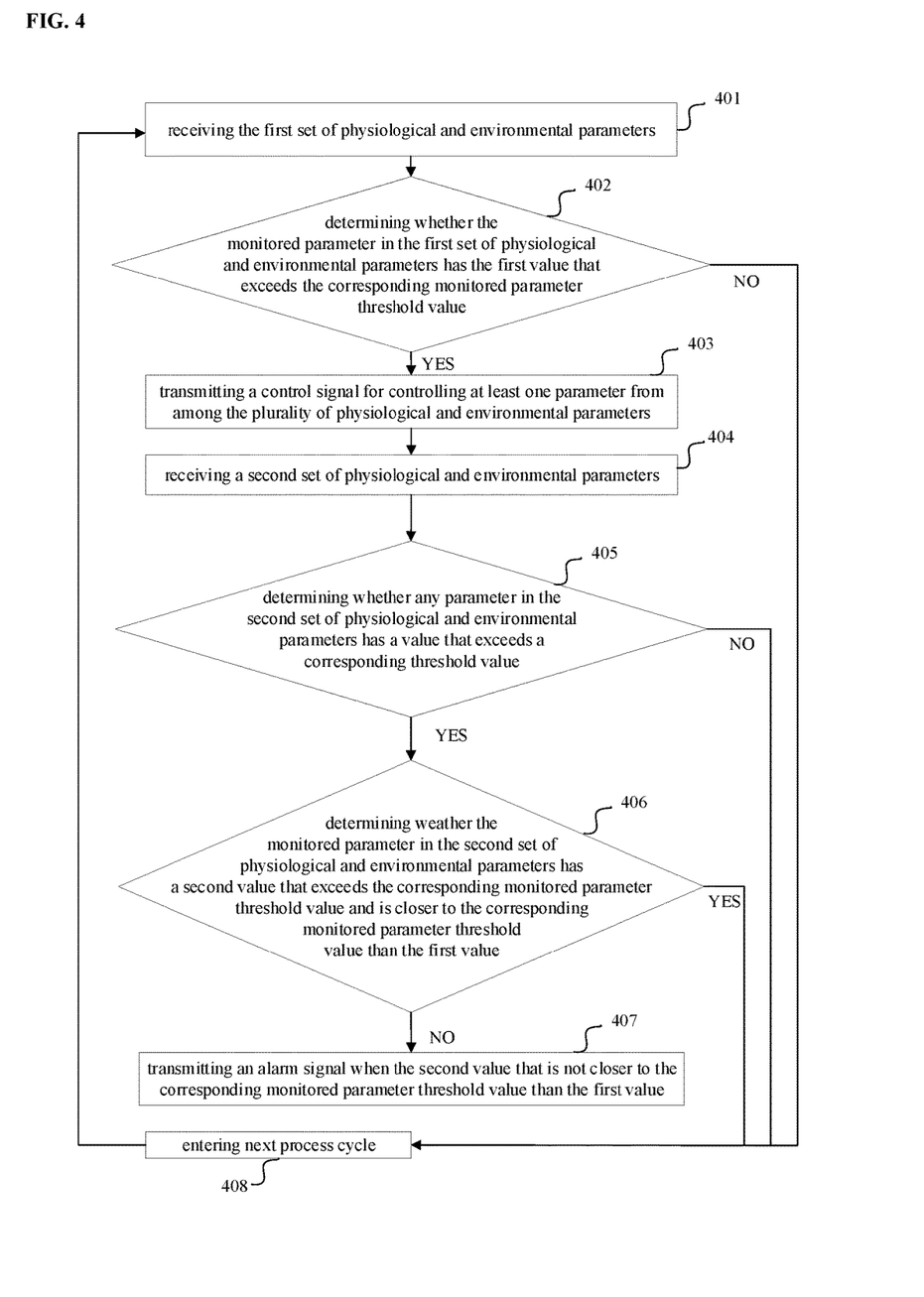
FIG. 4 is a flow chart illustrating the operating process of a controller in some embodiments according to the present disclosure.

FIG. 4 is a flow chart illustrating the operating process of a controller in some embodiments according to the present disclosure. Optionally, the controller in FIG. 4 is configured to be coupled with a vehicular safety seat in FIG. 3. Referring to FIG. 4, the process in some embodiments includes a step 401 of receiving the first set of physiological and environmental parameters. For example, the process may include receiving from the first transmitter in the vehicular safety seat by the second receiver in the controller the first set of physiological and environmental parameters.

Next, the process includes a determination step 402 of determining whether the passenger is in a comfortable state. For example, the determination step may include determining whether a monitored parameter in the first set of physiological and environmental parameters has the first value that exceeds the corresponding monitored parameter threshold value. Optionally, the determination step further includes comparing the first set of physiological and environmental parameters with a set of threshold physiological and environmental parameters.

If the monitored parameter in the first set of physiological and environmental parameters has the first value that exceeds the corresponding monitored parameter threshold value (e.g., the passenger is not in a comfortable state), the process further includes a step 403 of transmitting a control signal for controlling at least one parameter from among the plurality of physiological and environmental parameters, e.g., to a vehicular safety seat. Optionally, the process further includes transmitting an alert signal to the driver, indicating that the passenger is not in a comfortable status, e.g., one or more monitored parameter exceeds the corresponding monitored parameter threshold value.

In some embodiments, the process further includes a step 404 of receiving a second set of physiological and environmental parameters, e.g., from a first transmitter in the vehicular safety seat of FIG. 3. Optionally, the second set of physiological and environmental parameters are detected by the detector in the vehicular safety seat and transmitted by the first transmitter in the vehicular safety seat at the second time interval after the adjustor in the vehicular safety seat adjusts the at least one of the plurality of environmental parameters.

The process further includes a determination step of determining whether the passenger is in a comfortable state. For example, the determination step may include a step 405 of determining whether any parameter in the second set of physiological and environmental parameters has a value that exceeds a corresponding threshold value. Optionally, the determination step further includes comparing the second set of physiological and environmental parameters with the set of threshold physiological and environmental parameters and the first set of physiological and environmental parameters. If it is determined that the passenger is in a comfortable state, e.g., none of the parameters in the second set of physiological and environmental parameters has a value that exceeds the corresponding threshold value, then the process enters into the next process cycle, e.g., repeating the step of receiving the first set of physiological and environmental parameters.

If it is determined that the passenger is not in a comfortable state, e.g., at least one parameter in the second set of physiological and environmental parameters has a value that exceeds the corresponding threshold value, the process further includes a determination step 406 of determining whether the monitored parameter in the second set of physiological and environmental parameters although still has a second value that exceeds the corresponding monitored parameter threshold value but is closer to the corresponding monitored parameter threshold value than the first value. If the physiological or environmental parameters associated with the passenger are improved by the adjustment, e.g., the monitored parameter in the second set of physiological and environmental parameters has the second value that is closer to the corresponding monitored parameter threshold value than the first value, the process enters the next process cycle, e.g., repeating one or more steps described above. Optionally, if the he physiological or environmental parameters associated with the passenger are improved by the adjustment, the process further includes continuing adjusting the at least one of the plurality of environmental parameters.

If it is determined that the physiological or environmental parameters associated with the passenger are not improved by the adjustment, e.g., the monitored parameter in the second set of physiological and environmental parameters has the second value that is not closer to the corresponding monitored parameter threshold value than the first value, the process further includes a step 407 of transmitting an alarm signal when the second value that is not closer to the corresponding monitored parameter threshold value than the first value, e.g., to a driver or another passenger. The alarm may be transmitted in any appropriate forms, e.g., a voice message, an alarm sound, an image, etc. Optionally, the process further includes a step 408 of entering into the next process cycle after the alarm is transmitted, e.g., repeating one or more steps described above.

In determining whether the physiological or environmental parameters associated with the passenger are improved by the adjustment, the attributes of each individual parameter should be taken into account. For example, in some embodiments, whether the physiological or environmental parameters associated with the passenger are improved can be determined by comparing the second set of physiological and environmental parameters with the set of threshold physiological and environmental parameters and the first set of physiological and environmental parameters, and checking whether the monitored parameter in the second set of physiological and environmental parameters has a second value that exceeds the corresponding monitored parameter threshold value and is closer to the corresponding monitored parameter threshold value than the first value. In one example, the monitored parameter is the passenger's surface temperature. The corresponding monitored parameter threshold value would be a normal surface temperature of an individual, e.g., 36.5 Celsius degrees. The closer the surface temperature in the second set to 36.5 Celsius degrees, the greater improvement on the physiological or environmental parameters associated with the passenger the adjustment achieves. In another example, the monitored parameter threshold value includes a first threshold value as an upper limit of a range of optimal values, and a second threshold value as a lower limit of the range of optimal values. When the monitor parameter has a value that is higher than the first threshold value or lower than the second threshold value, it exceeds the threshold value. In another example, the monitored parameter is the ambient temperature. The first threshold value may be 22 Celsius degrees, and the second threshold value may be 20 Celsius degrees. When the monitored parameter gets closer to either the first threshold value (e.g., decreasing from 24 Celsius degrees to 23 Celsius degrees) or the second threshold value (e.g., increasing from 18 Celsius degrees to 19 Celsius degrees), the ambient temperature parameter is considered to have been improved by the adjustment.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A vehicular safety seat for a passenger, comprising:
a detector configured to detect a plurality of physiological parameters and a plurality of environmental parameters associated with the passenger;
a first transmitter configured to transmit a first set of physiological and environmental parameters detected by the detector;
a first receiver configured to receive a control signal for controlling at least one parameter from among the plurality of physiological and environmental parameters based on a determination that a monitored parameter in the first set of physiological and environmental parameters has a first value that exceeds a corresponding monitored parameter threshold value;
an adjustor configured to adjust a specifically monitored environmental parameter of the plurality of environmental parameters based on the control signal; and
a head rest for supporting at least a portion of the passenger's head and neck, provided on a seat back of the vehicular safety seat;
wherein the detector is configured to detect a second set of physiological and environmental parameters at a second time interval after the adjustor adjusts the specifically monitored environmental parameter of the plurality of environmental parameters;
the first transmitter is configured to transmit the second set of physiological and environmental parameters;
the adjustor is configured to continue adjusting the specifically monitored environmental parameter of the plurality of environmental parameters based on a determination that the monitored parameter in the second set of physiological and environmental parameters has a second value that exceeds the corresponding monitored parameter threshold value, and is closer to the corresponding monitored parameter threshold value than the first value;
the detector comprises a first temperature sensor configured to sense a skin temperature of the passenger, and a second temperature sensor configured to sense an ambient temperature;
the first temperature sensor is on a first surface of the head rest configured to be at least partially in contact with the passenger's neck; and
the second temperature sensor is on a second surface beside the first surface of the head rest configured to have no contact with the passenger;
the adjustor comprises one or more of a temperature adjustor, a music player, a tension adjustor, and a dryer;
the temperature adjustor comprises an air ventilating apparatus on a side surface of a seat back of the vehicular safety seat; and
the specifically monitored environmental parameter is selected from a group consisting of ambient temperature, ambient sound level, tension of a vehicular seat belt, and ambient humidity.

2. The vehicular safety seat of claim 1, wherein the first transmitter is configured to transmit the first set of physiological and environmental parameters at every first time interval.

3. The vehicular safety seat of claim 1, wherein the detector comprises a sound sensor for sensing a volume level of sound in the passenger's vicinity; and
the first transmitter is configured to transmit the first set of physiological and environmental parameters when the volume level of sound in the passenger's vicinity exceeds a threshold volume level.

4. The vehicular safety seat of claim 1, wherein the detector comprises one or more of a temperature sensor, a humidity sensor, a heart rate sensor, and a pressure sensor.

5. The vehicular safety seat of claim 1, wherein the detector comprises a camera configured to obtain an image of the passenger.

6. A controller configured to be coupled with a vehicular safety seat of claim 1, comprising:
a second receiver configured to receive from the first transmitter the first set of physiological and environmental parameters;
a processor configured to compare the first set of physiological and environmental parameters with a set of threshold physiological and environmental parameters, and determine whether the monitored parameter in the first set of physiological and environmental parameters has the first value that exceeds the corresponding monitored parameter threshold value; and a second transmitter configured to transmit the control signal to the first receiver;

wherein the detector is configured to detect a second set of physiological and environmental parameters at a second time interval after the adjustor adjusts the specifically monitored environmental parameter of the plurality of environmental parameters;

the first transmitter is configured to transmit to the second receiver the second set of physiological and environmental parameters;

the second receiver is configured to receive from the first transmitter the second set of physiological and environmental parameters;

the processor is configured to compare the second set of physiological and environmental parameters with the set of threshold physiological and environmental parameters, and determine whether any parameter in the second set of physiological and environmental parameters has a value that exceeds a corresponding threshold value; and the processor is configured to compare the second set of physiological and environmental parameters with the set of threshold physiological and environmental parameters and the first set of physiological and environmental parameters, and determine whether the monitored parameter in the second set of physiological and environmental parameters has a second value that exceeds the corresponding monitored parameter threshold value and is closer to the corresponding monitored parameter threshold value than the first value.

7. The controller of claim 6, wherein the second transmitter is configured to transmit an alarm signal when the second value that is not closer to the corresponding monitored parameter threshold value than the first value.

8. The controller of claim 6, further comprising a display panel configured to display a current set of physiological and environmental parameters associated with the passenger, and an indication whether any parameter in the current set of physiological and environmental parameters exceeds a corresponding threshold value.

9. The controller of claim 6, wherein the controller is integrated into a mobile apparatus or a vehicle-mounted electronic system.

* * * * *